United States Patent [19]

Shudo

[11] Patent Number: 4,831,052
[45] Date of Patent: May 16, 1989

[54] FLAVONE CARBOXYLIC ACID DERIVATIVES

[75] Inventor: Koichi Shudo, Tokyo, Japan

[73] Assignee: Shionogi & Co., Ltd., Osaka, Japan

[21] Appl. No.: 27,324

[22] Filed: Mar. 18, 1987

[30] Foreign Application Priority Data

Mar. 18, 1986 [JP] Japan ................................. 61-59850

[51] Int. Cl.$^4$ .................... A61K 31/35; C07D 311/92; C07D 311/78
[52] U.S. Cl. .................................. 514/455; 549/389; 549/392
[58] Field of Search ................. 549/389, 392; 514/455

[56] References Cited

FOREIGN PATENT DOCUMENTS 1461777  1/1977  United Kingdom .

OTHER PUBLICATIONS

Fisons, C. A., 83, 9792f (1975)—Abstract of Neth. Appl. 7407,648.
J. Med. Chem. 1980, 23, 335–338.

Primary Examiner—Nicky Chan
Attorney, Agent, or Firm—Gordon W. Hueschen

[57] ABSTRACT

Novel flavone carboxylic acid derivatives, intermediates therefor, and method for the preparation thereof, and their use in the differentiation of certain types of malignant cells, are all disclosed, certain of the novel compounds disclosed to be superior to retinoic acid in their activity.

7 Claims, No Drawings

FLAVONE CARBOXYLIC ACID DERIVATIVES

FIELD OF THE INVENTION

The present invention relates to novel organic compounds which are potentially useful medicaments and which should be further developed and offered for therapeutic use.

In the literature "Cancer Chemotherapy and Pharmacology" (1981) it has been described that Arotinoids are a new class of Retinoids having particularly interesting biological properties and that Arotinoid Ro 13 6298, which can be regarded as a Retinoic acid derivative, leads in minute quantities to regression of chemically induced papillomas of the skin of mice and also has a therapeutic influence on chemically-induced skin carcinomas in mice.

Further, from "Retinoids at the Threshold", J. Med. Chem. 25, 1269–1277(1982), it is known that Arotinoid has an activity which is ten times as strong as that of Retinoic acid (as seen from the therapeutic index (see Page 1271 of the literature).

In German Patent Application No. P 35 24 199.3 of the applicant, it has been disclosed that the effect in the treatment of tumors of cetain stilbene compounds represented by formula (I)

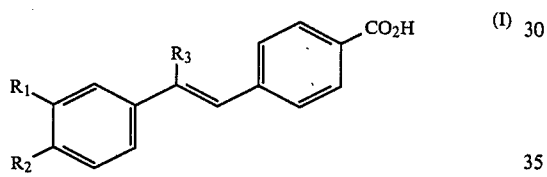

is far superior to Retinoic acid and Artinoids, which contain the retinol carbon skeleton in rigid conformeric fixation because of the presence of two aromatic rings, and established that compounds of the formula I, although not possessing the end ring structure of the Vitamin A molecule, could and do have the same antitumor effect and therapeutic effect on skin diseases as compounds which do possess the Vitamin A structure.

Another previous patent application of the applicant, (European Patent Application No. 85 108 383.2) discloses that benzoic acid derivatives represented by formula (II)

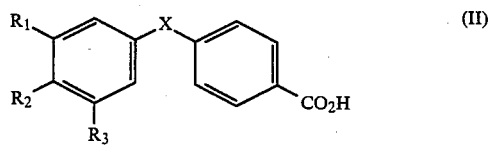

wherein $R_1$ and $R_2$ represent alkyl or cycloalkyl, and X represents a group of the formula —NHCO—, —CONH—, —N=N—, or —COCH=CH—, exhibit the same antitumor activity as the compounds represented by formula I, and are structurally characterized by the presence of (a) two phenyl groups combined by a linking chain, such as —NHCO—, —CONH—, —N=N—, or —COCH=CH—, (b) a carboxyl group in para position of one phenyl group, and (c) middle alkyl group(s) such as isopropyl or the like on the other phenyl group, this third characteristic being most important for the effect of the compounds of the formula (II).

On the other hand, a compound having the formula

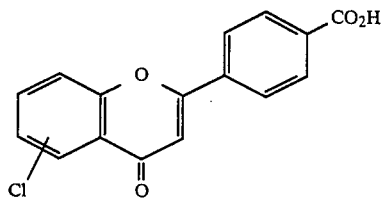

is already reported in Brit. Pat. Appl. No. 27379/73; C.A. 83 p9792f.

DETAILED DESCRIPTION OF THE INVENTION

It has now been found that flavone carboxylic acid derivatives represented by the formula (III):

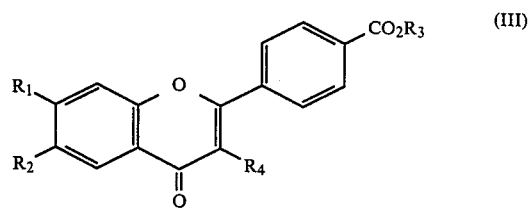

wherein $R_1$ and $R_2$ may be the same or different and each represents hydrogen or lower-alkyl, especially lower-alkyl having 3C or 4C, at least one of $R_1$ and $R_2$ being other than hydrogen, and wherein both neighboring $R_1$ and $R_2$ may be combined together optionally with an oxygen, nitrogen, or sulfur atom to form a 5 or 6 membered heterocycle or cycloalkyl, which is optionally but preferably substituted with lower alkyl(s), $R_3$ represents hydrogen or lower alkyl, and $R_4$ represents hydrogen or hydroxyl, as well as intermediates represented by formula (IV):

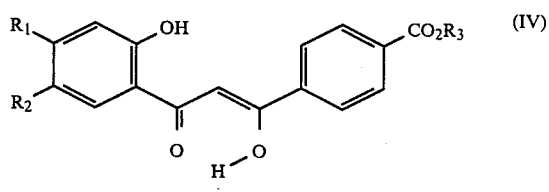

for preparing the carboxylic acid derivatives (III; $R_4$=H), as well as intermediate (V):

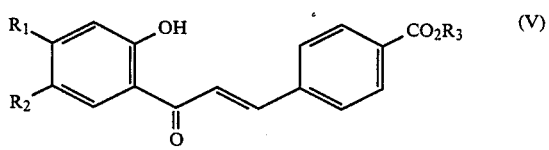

for preparing III; $R_4$=OH), are all capable of inducing the differentiation of malignant cells, especially leukemia cells, morphologically and functionally, and can therefore be used for the treatment of tumors and cancers, leukemia, T cell malignant diseases, and malignant dermatological diseases, in the same manner as the compounds represented by formulas (I) and (II).

The test of the activities of the compounds of this invention has been conducted by measuring the concentration required for inducing the differentiation of human acute promyelocytic leukemia cells HL 60, according to the methods described in detail hereinafter.

Test Procedures

The compounds of the invention are tested according to established test procedure which shows the differentiation of malignant cells, whereby the differentiation of human acute promyelocytic leukemia cells (HL-60) and their conversion to granulocytes (myelocytes) is assayed by an observation of the morphological changes of nuclei and by the measurement of the degree of reduction of nitro-blue tetrazolium (NBT) which is induced by a test compound (Proc. Natl Acad. Sci. USA 77, 2936–2940 (1980) with the Title: Induction of differentiation of the human promyelocytic leukemia cell line (HL-60) by retinoic acid).

The HL-60 cell are cultured in plastic flasks in RPMI 1640 medium supplemented with 5% heat inactivated fetal calf serum and antibiotics (penicillin G and streptomycin). The cells ($3 \times 10^4$/ml) are cultured with a compound of the present invention for 4 days. The cells are fixed and stained with Wright-Giemsa to examine the morphological changes of the nuclei.

The cells treated with the compounds of the present invention are differentiated to mature granulocytes (myelocytes, metamyelocytes and neutrophiles), just as the cells treated with retinoic acid.

The biochemical activity of cells treated with the compound is measured as follows:

The cells after 5 days incubation are centrifuged and diluted with RPMI 1640 medium, supplemented with 5% fetal calf serum to provide a definite number of the cells. To the diluted cell suspension are then added 200 ng/ml of 12-o-tetradodecanoylphorbol-13-acetate (TPA) and the resulting culture medium is then incubated for 20 minutes at 37° C. in the presence of 0.1% of NBT. Thus, the mature differentiated cells containing blue-black formazan is counted by microscopy, so that the ratio of the cells having the ability to reduce NBT, to total cells, can be calculated.

The cells treated with the compounds of this invention show the NBT reduction activity which corresponds to the important biochemical activity of differentiated cells.

The results of the tests according to the above-mentioned methods are summarized in Table 1.

Since the compounds of the present invention differentiate the leukemia cells to mature granulocytes morphologically and functionally, they can be used as medicines to use for treatment of humans and animals with cancer and dermatological disorders, and further as diagnosis for determining the type of leukemia by a measuring method, whereby the blood of a patient with leukemia is incubated in vitro in the presence of a present compound in an analogous manner as described in the morphological assay for the HL 60 cells: Only promyelocytic leukemia cells, but not lymphocytic leukemia cells, differentiate to mature granulocytes which can be clearly determined by microscope (See: Saibo (Cells 14,533 (1982).

When the incubation is performed in a soft agar, promyelocytic leukemia cells do not form a colony, since the differentiated cells do not proliferate further.

Thus, these compounds are very useful in the determination of promyelocytic leukemia, which enables the selection of a proper therapeutical method of approach.

These compounds also suppress the hyperkeratinization of human tissue cells, and are useful for the treatment of cystic acne, psoriasis, and related cutaneous disorders of keratiniztion and of epithelial differentiation As shown in Table 1, the activity of the compounds of this invention is observed at a concentration lower than $10^{-6}$ Mol Those compounds with strongest activity show the effect even at a concentration of $10^{-8}$ to $10^{-11}$. From Table 1 it is clear that a compound represented by the formula (III), wherein $R_1$ and $R_2$ are both hydrogen; does not exhibit the desired activity, while the compounds wherein $R_1$ and $R_2$ mean lower-alkyl exhibit the desired activity. The presence of alkyl group(s) is therefore crucial for the appearance of the activity, as has been previously shown in the case of compounds of Formula (II) by the present applicant. The compounds of the formula (III), wherein $R_1$ and $R_2$ mean a medium alkyl group, such as an isopropyl or tert. butyl, preferably a six-membered cycloalkyl group in which they are combined, exhibit the strongest activity. In particular, compound (VI) of the formula:

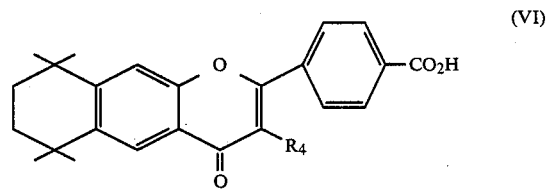

is one of the strongest compounds.

Intermediates (IV) and (V), for preparing the compounds (III) ($R_4$=H) and III($R_4$=OH) respectively, also exhibited strong activity towards human leukemia cells at concentrations lower than retinoic acid and arotinoid. In these cases, substituents $R_1$ and $R_2$ are very important, and especially the cyclic (IV) ($R_1$, $R_2$=(CH$_3$)$_2$CCH$_2$CH$_2$C(CH$_3$)$_2$, $R_3$=H) is most active compound (VII):

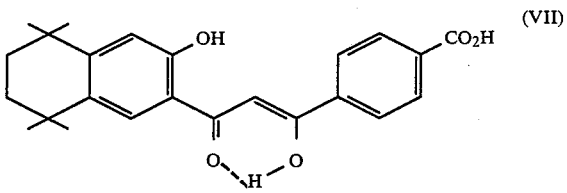

The compounds (IV) are enol forms of benzoylacetophenones, which exist in equilibrium with the other enol forms (IVa):

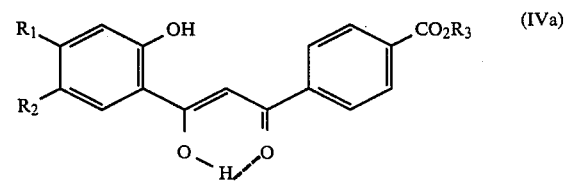

For the therapy of cancer such as T cell lymphoma, acute promyelocytic leukemia, neuroblastoma, and carcinoma, the compounds of this invention can be used systemically, for example by injection or oral administration, in an amount of less than 5 mg/Kg/day, preferably 0.001–1 mg/Kg/day and, for therapy of psoriasis and other dermatological diseases, topically for example as ointments containing the compound itself or a mixture with other medicaments such as a corticosteroid, anthrarine, and UV therapeutica, in an amount of 0.1–10 mg of the active compound per gram of ointment.

Flavone-4'-carboxylic acid derivatives represented by the formula (III;$R_4$=H) can be prepared from a terephthalic acid derivative of the formula (VIII):

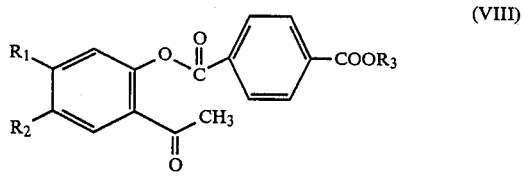

(VIII)

Compound (VIII) was treated with alkali hydroxide in a basic solvent such as pyridine to give an intermediate represented by the formula (IV) shown above. This enol compound is heated with sulfuric acid in acetic acid to yield the desired compound(III; $R_3$=alkyl). If necessary, this ester can be hydrolysed in the usual manner to give the flavone 4'-carboxylic acid(III; $R_3$=H, $R_4$=H).

Flavone-4'-carboxy acids (III, $R_4$=OH) was prepared from chalcone derivatives (V) by treatment with hydrogen peroxide in alkaline medium.

The following examples are given by way of illustration only and are not be constructed as limitations of this invention.

EXAMPLE 1

Preparation of Compound
III($R_1$=tBu,$R_2$=$R_3$=$R_4$=H) (No.2)

To a solution of 2.0 g of m-tert.-butylphenol in 30 ml of pyridine was added 1.05 g of acetylchloride under ice cooling and the mixture was stirred at room temperature for 2–3 hours. After distillation of pyridine and extraction by ether, the ether layer was washed with water, Cu(NO$_3$)$_2$aq, water, saturated saline solution, and dried over MgSO$_4$. The solvent was distilled off to give 2.3 g of the acetate (yield; 89.9%).

Then 495 mg of acetate obtained as above were melted by warming and, after addition of 360 mg of AlCl$_3$, were heated at 145° C. After ten minutes, ice was added to the reaction mixture, and the solution was extracted with ether. The resulting organic layer was washed with water until the pH of the washing showed 7, and then dried over MgSO$_4$. The distillation of the solvent and purification by chromatography through silica gel column (CH$_2$Cl$_2$:n-hexane, 1:1) gave 337 mg of 4-tert.-butyl-2-hydroxyacetophenone (yield: 68.1%).

To a solution of 1.07 g of the thus-obtained 4-tert.-butyl-2-hydroxyacetophenone in 10 ml of pyridine was added 1.125 g of terephthalic acid monomethylester chloride and the mixture stirred at room temperature for one night. The reaction mixture was diluted with ethyl acetate and washed with water, Cu(NO$_3$) 0.2aq, water, aqueous solution of sodium hydrogencarbonate, and saturated saline solution, and then dried over MgSO$_4$. The distillation of the solvent and purification by chromatography through silica gel column gave 900 mg of the derivative of terephthalic acid methylester (yield: 45.6%). The recrystallized product from methylenechloride-hexane has a m.p. of 95.5°–96° C.

To a solution of 257 mg of the thus-obtained methylester in 5 ml of pyridine were added 100 mg of KOH and the mixture was stirred at room temperature for one night. The reaction mixture was poured over 20 ml of 20% acetic acid and the resulting crystalline solid was extracted in ethyl acetate. The organic layer was washed with water 2–3 times and dried over MgSO$_4$. The distillation of the solvent and purification by chromatography through silica gel column gave 180 mg of the rearranged product ( IV, $R_1$=tBu, $R_2$=H, $R_3$=CH$_3$) (yield: 70.0%), as pale yellow plate having a melting point of 144°–145.5° C. (recrystallized from CH$_2$Cl$_2$- hexane).

To a solution of 40 mg of the thus-obtained rearranged product in 4 ml of acetic acid was added 0.1 ml of sulfuric acid and the mixture was refluxed for 15 minutes, poured over water, and extracted with ethyl acetate. The resulting organic layer was washed with water, 1N sodium hydrogencarbonate, water, saturated saline solution, and dried over MgSO$_4$. The distillation of the solvent and purification by chromatography through silica gel column gave 31 mg (yield: 81.7%) of the flavone carboxylic acid ester (III: $R_1$=tBu, $R_2$=H, $R_3$=CH$_3$) as colorless needles having a melting point of 183°–185 ° C. (recrystallized from methylene chloride-hexane).

To a solution of 50 mg of the thus-obtained flavone carboxylic acid ester in 5 ml of 95% ethyl alcohol was added a 0.15M solution of caustic potash in 1 ml of ethanol and the mixture stirred at room temperature for one night. The reaction mixture was poured over dilute hydrochloric acid, adjusted to pH 7, and extracted with ethyl acetate. The extracted solution was washed with water until the pH of the washing became 7 and dried over MgSO$_4$. The solvent was removed to give the flavone carboxylic acid (III, $R_1$=tBu, $R_2$=H, $R_3$=H: No. 2), as pale yellow plate having a melting point of 284.5°–285.5° C.

EXAMPLE 2

Preparation of Compound ($R_1$,$R_2$=(CH$_3$)$_2$C(CH$_2$CH$_2$) O, $R_3$=$R_4$=H; No.3)

(a) 1.084 g of acetophenone represented by the formula:

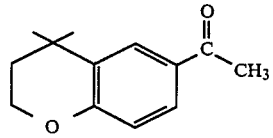

were dissolved in 30 ml of chloroform, 1.6 g of m-chloroperbenzoic acid (mCPBA) added and the mixture was refluxed for 4 hours. The reaction solution was cooled and the insoluble materials were removed by filtration. The concentrated filtrate was treated by chromatography through silica gel (CH$_2$Cl$_2$:n-hexane) and gave 755 mg (yield: 64.6%) of acetate.

To a solution of 755 mg of the thus-obtained acetate in nitrobenzene were added 456 mg of finely divided AlCl$_3$, and the mixture was heated for one hour at 120°–125° C. The reaction mixture was diluted by water and extracted with ethyl acetate. The extracted solution was washed with water, sodium hydrogencarbonate solution, water, and saturated saline solution in series and dried over MgSO$_4$. The distillation of the solvent and purification by chromatography through silica gel column gave 490 mg (yield: 64.9%) of the 2-hydroxyacetophenone.

To a solution of the thus-obtained 112 mg of 2-hydroxyacetophenone in 10 ml of pyridine was added 300 mg of terephthalic acid monomethyl ester chloride and the mixture stirred at room temperature for one night. The reaction mixture was diluted with ethyl acetate and washed with water, Cu(NO$_3$) 0.2 aq, water, sodium bicarbonate solution, saturated saline solution and dried over MgSO$_4$. The distillation of the solvent and purification by chromatography through silica gel column gave 161 mg (yield: 82.8%) of the derivative of terephthalic acid methylester. To a solution of 257 mg of the thus-obtained methylester in 5 ml of pyridine was added 75 mg of caustic potash and the mixture stirred at room temperature for one night. The reaction mixture was poured over 20 ml of 20% acetic acid and extracted in ethyl acetate. The resulting organic layer was washed with water 2-3 times and dried over MgSO$_4$. The distillation of the solvent and purification by chromatography through silica gel column gave 135 mg (yield: 62.8%) of the rearranged product (IV, R$_1$, R$_2$=(CH$_3$)$_2$CCH$_2$CH$_2$O, R$_3$=CH$_3$, as orange needles having a melting point of 193°–195.5° C. (CH$_2$Cl$_2$-hexane).

(b) To a solution of 60 mg of the thus-obtained transformer in 5 ml of acetic acid was added 0.1 ml of sulfuric acid and the mixture refluxed for 30 minutes. The reaction mixture was then poured over water and extracted with ethyl acetate. The resulting organic layer was washed with water, 1N sodium hydrogencarbonate, water, saturated saline solution and dried over MgSO$_4$. The distillation of the solvent and purification by chromatography through silica gel column gave 35 mg (yield: 61.2%) of the flavone carboxylic acid ester-(III, R$_1$, R$_2$=(CH$_3$)$_2$CCH$_2$CH$_2$O, R$_3$=CH$_3$,R$_4$=H) as colorless prisms having a melting point of 195.5°–196.5° C. (recrystallized from methylene chloride/hexane).

To a solution of 35 mg of the thus-obtained flavone carboxylic acid methylester in 3 ml of ethyl alcohol were added 0.15M solution of caustic potash in 0.65 ml ethanol and the mixture stirred at room temperature for one night. To the reaction mixture was added dilute hydrochloric acid and the solution was adjusted to pH 7 and extracted with ethyl acetate. The extracted solution was washed with water until the pH of the washing became 7 and dried over MgSO$_4$. The solvent was removed to give the flavone carboxylic acid (III; R$_1$, R$_2$=(CH$_3$)$_2$CCH$_2$CH$_2$O,R$_3$=H,R$_4$=H; No. 3) as colorless prisms having a melting point of higher than 300° C. (from methanol).

EXAMPLE 3

III(R$_1$,R$_2$=(CCH$_3$)$_2$CCH$_2$CH$_2$C(CH$_3$)$_2$, R$_3$=R$_4$=H; No. 5;

4-(6,7,8,9-tetrahydro-6,6,9,9-tetramethyl-4H-4-oxonaphtho[2,3-b]pyran-2-yl) benzoic acid (6,7-(1,1,4,4-tetramethylbutano) flavone-4'-carboxylic acid 5.01 g of acetophenone represented by the formula:

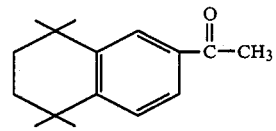

were dissolved in 30 ml of chloroform, 8.0 g of mCPBA was added, and the mixture was refluxed for 4 hours. The reaction mixture was diluted into methylene chloride and washed with water, sodium bicarbonate, water, saturated saline solution and dried over MgSO$_4$. The distillation of the solvent and purification by chromatography through silica gel column gave 3.9 g(yield: 72.8%) of acetate. To a solution of 570 mg of acetate thus obtained in 8 ml of nitrobenzene were added 320 mg of AlCl$_3$, and the mixture was heated for 2 hours at 120° C. The reaction mixture was poured over water and extracted in ethyl acetate. The extracted solution was washed with water, sodium hydrogencarbonate, water, saturated saline solution and dried over MgSO$_4$. The distillation of the solvent, evaporating of nitrobenzene, and purification by chromatography through silica gel column gave 320 mg (yield: 56.1%) of o-hydroxyacetophenone as a colorless oil.

To a solution of 448 mg of the thus-obtained o-hydroxyacetophenone in 6 ml of pyridine was added 1.6 g of terephthalic acid monomethylester chloride and the mixture stirred at room temperature for one night. The reaction mixture was poured over water and extracted with ethyl acetate and washed with dilute hydrochloric acid, water, 1N hydrogencarbonate, water, saturated saline solution and dried over MgSO$_4$. The distillation of the solvent and purification by chromatography through silica gel column gave 600 mg (yield: 80.0%) of the derivative of terephthalic acid methyl ester. To a solution of 210 ml of the thus-obtained methylester in 5 ml of pyridine was added 70 mg of caustic potash and the mixture stirred at room temperature for one night. The reaction mixture was poured over 30 ml of 20% acetic acid and then extracted in ethyl acetate. The organic layer was washed with water 2-3 times and dried over MgSO$_4$. The distillation of the solvent and purification by chromatography through silica gel column gave 112 mg (yield: 53.3%) of the rearranged product (IV; R$_1$, R$_3$=(CH$_3$)$_2$CCH$_2$(CH$_3$)$_2$, R$_3$=CH$_3$) as pale yellow needles having a melting point of 161°–162 ° C. when crystallized from CH$_2$Cl$_2$/hexane.

(b)To a solution of 80 mg of the thus obtained rearranged product in 5 ml of acetic acid was added 0.2 ml of sulfuric acid and the mixture refluxed for 30 minutes, whereafter the reaction mixture was poured into water and extracted with ethyl acetate. The resulting organic layer was washed with water until the pH of the washing became 7 and dried over MgSO$_4$. The distillation of the solvent and purification by chromatography through silica gel column gave 32 mg (yield: 41.8%) of the flavone carboxylic acid ester(III; R$_1$, R$_2$=(CH$_3$)$_2$CCH$_2$CH$_2$C(CH$_3$)$_2$,R$_3$=CH$_3$,R$_4$=H;No.4) as colorless flakes having a melting point of 175°–176° C. (recrystallized from methylenechloride/hexane).

To a solution of 50 mg of the thus-obtained flavone carboxylic acid ester in 4 ml of ethyl alcohol was added a 0.15M solution of caustic potash in 0.85 ml ethanol and the mixture stirred at room temperature for one night. To the reaction mixture was then added dilute hydrochloric acid, the solution adjusted to pH 7 and extracted with ethyl acetate. The extracted solution was washed with water until the pH of the washing became 7 and dried over MgSO4. The solvent was removed to give the flavone carboxylic acid (III; $R_1$, $R_2$=$(CH_3)_2CCH_2CH_2C(CH_3)_2$, $R_3$=$R_4$=H;No.5), as colorless prism columns (from methanol) having a melting point more than 300° C.

EXAMPLE 4

Preparation of V($R_1$, $R_2$=$(CH_3)_2CCH_2CH_2C(CH_3)_2$, $R_3$=H; No.7;
4-[3-(3-hydroxy-5,6,7,8-tetrahydro-5,5,8,8-tetramethyl-2-naphthalenyl)-3-oxo-1-propenyl]benzoic acid, and III($R_1$,$R_2$=$(CH_3)_2CCH_2CH_2C(CH_3)_2$, $R_3$=H, $R_4$=OH; No.6;
4-(6,7,8,9-tetrahydro-6,6,9,9-tetramethyl-3-hydroxy-4H-4-oxo- naphtho[2,3-b]pyran-2-yl)benzoic acid (3-hydroxy-6,7-(1,1,4,4-tetramethylbutano) flavone-4'-carboxylic acid))

To a solution of the o-hydroxyacetophenone (1.0 g) obtained in Example 3 and terephthalaldehydic acid methyl ester (670 mg) in EtOH (20 ml) was added 10 ml of 2N NaOH, and the mixture was stirred for a night at room temperature. Acidification by dilute HCl yielded a yellow precipate (1.2 g), which was recrystallized from AcOEt-EtOH, m.p. 267°–269° C. (V: $R_1$, $R_2$=$(CH_3)_2CCH_2CH_2C(CH_3)_2$, $R_3$=H; Compound No.7).

To a suspension of V (0.215 g) obtained in CH3OH (12 ml) was added 4 ml of 2N NaOH under ice cooling. To the resultant solution, 0.8 ml of 30% $H_2O_2$ was added dropwise, and the mixture was kept in a refrigerator for one night. After pouring the solution into dilute HCl, the mixture was extracted with AcOEt, and the organic layer was washed with water and dried over MgSO4. After evaporation of the solvent, the product was recrystallized from AcOEt to give yellow prisms (III, $R_1$, $R_2$=$(CH_3)_2CCH_2CH_2C(CH_3)_2$, $R_3$=H, $R_4$=OH; compound No. 6) m.p. 298°–300° C.

EXAMPLE 5

Preparation of IV ($R_1$, $R_2$=$(CH_3)_2CCH_2CH_2C(CH_3)_2$, $R_3$=H; No.8;
4-[1-hydroxy-3-(3-hydroxy-5,6,7,8-tetrahydro-5,5,8,8-tetra-methyl-2-naphthalenyl)-3-oxo-1-propenyl]benzoic acid (equivalent to 4-[1-(3-hydroxy-5,6,7,8-tetrahydro -5,5,8,8-tetramethyl-2-naphthalenyl-1-oxo-3-hydroxy-2-propenyl]benzoic acid)

To a methanol solution of 250 mg of the intermediate methyl ester (IV, $R_1$, $R_2$=$(CH_3)_2CCH_2CH_2C(CH_3)_2$, $R_3$=CH3) obtained in Example 3 was added 1N NaOH (10 ml), and the mixture was stirred for 5 hours at room temperature. Dilution with dilute HCl yielded a yellow precipitate (0.2 g), which was recrystallized from ethanol to give plates, m.p. 232°–233° C. (IV: $R_1$, $R_2$=$(CH_3)_2,CCH_2CH_2C$ $(CH_3)_2$, $R_3$=H; Compound No.8).

EXAMPLE 6

Preparation of IV ($R_1$=tBu, $R_2$=H, $R_3$=H; No. 9)

To a methanol solution of 100 mg of the intermediate methyl ester (IV, $R_1$=tBu, $R_2$=H, $R_3$=CH3, $R_4$=H) obtained in Example 1 was added 1N NaOH (5 ml), and the mixture was kept for 5 hours at room temperature. Acidification of the solution by dilute HCl yielded a yellow precipitate, which was recrystallized from ethanol to give IV (IV: $R_1$=tBu, $R_2$=H, $R_3$=H: compound No.9) m.p. 245°–247° C.

EXAMPLE 7

Preparation of IV ($R_1$=H, $R_2$=t Bu, $R_3$=H; No. 10)

In a manner similar to Examples 1 and 6, IV ($R_1$=H, $R_2$=t Bu, R=H; No. 10) was prepared starting from 4-t-butyl-3acetylphenol, via the corresponding terephthalic acid ester and recrystallized from ethanol to give a yellow crystalline solid, m.p. 199°–200° C.

Biological activity

The biological test was performed according to the method previously described, using the leukemia cells HL 60. The morphological changes were observed under a light microscope. Biochemical activity reducing nitro-blue tetrazolium is assayed by counting the number of cells which contain formazan. The specific activity, $ED_{50}$ (the concentration which causes the differentiation of 50% of the total cells, represented by M), was calculated and shown in the Table. As a positive control for comparison, all trans retinoic acid was used.

The flavone carboxylic acid derivative wherein $R_1$ and $R_2$ represent isopropyl in formula (I), the sulfur derivative represented in Example 2, and the dihydroindan derivative represented in Example 3 are all synthesized by the same methods.

It is to be understood that the invention is not to be limited to the exact details of operation or exact compounds, compositions, methods, or procedures shown and described as obvious modifications and equivalents will be apparent to one skilled in the art.

TABLE 1

| No. | formula | $R_1$ | $R_2$ | $R_3$ | $R_4$ | $ED_{50}$ (M) |
|---|---|---|---|---|---|---|
| 1 | III | H | H | H | H* | inactive ($10^{-5}$) |
| 2 | III | t-Bu | H | H | H | $2.1 \times 10^{-7}$ |
| 3 | III | $(CH_3)_2CCH_2CH_2O$ | | H | H | $1.3 \times 10^{-7}$ |
| 4 | III | $(CH_3)_2CCH_2CH_2C(CH_3)_2$ | | $CH_3$ | H | $5.1 \times 10^{-10}$ |
| 5 | III | " | | H | H | $6.3 \times 10^{-11}$ |
| 6 | III | " | | H | OH | $1.2 \times 10^{-9}$ |
| 7 | V | " | | H | | $1.0 \times 10^{-10}$ |
| 8 | IV | " | | H | | $9.1 \times 10^{-11}$ |
| 9 | IV | t-Bu | H | H | | $9.3 \times 10^{-7}$ |
| 10 | IV | H | t-Bu | H | | $7.3 \times 10^{-8}$ |
| | retinoic acid (positive control) | | | | | $4.1 \times 10^{-9}$ |

$ED_{50}$: Effective doses which cause differentiation of 50% of the cultured cells, M(mol/l).

*this reference compound was prepared in a manner similar to the foregoing examples; m.p. 302–305° C.

What is claimed is:

1. A flavone carboxylic acid compound represented by the formula:

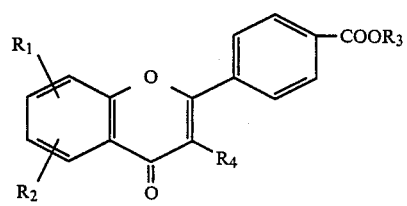

wherein $R_1$ and $R_2$ are in the 6,7-positions and are combined together optionally with an oxygen atom to form a 5-6 membered cycloalkyl or heterocycle, which must be substituted with at least two lower alkyl groups, $R_3$ represents hydrogen or lower alkyl, and $R_4$ represents hydrogen or hydroxyl.

2. Compound of claim 1 which is 4-(6,7,8,9-tetrahydro-6,6,9,9-tetramethyl-4H-4-oxo-naphtho[2,3-b]pyran-2-yl)benzoic acid (6,7-(1,1,4,4-tetramethylbutano)flavone-4'-carboxylic acid.

3. Compound of claim 1 which is 4-(6,7,8,9-tetrahydro-6,6,9,9-tetramethyl-3-hydroxy-4H-4-oxonaphtho[2,3-b]pyran-2-yl)benzoic acid (3-hydroxy-6,7-(1,1,4,4-tetramethylbutano)flavone-4'-carboxylic acid.

4. Compound of claim 1 which is methyl 4-(6,7,8,9-tetrahydro-6,6,9,9-tetramethyl-4H-oxo-naphtho/2,3-b/pyran-2-yl)benzoate.

5. Compound of claim 1 which is 4-(6,7,8,9-tetrahydro-9,9-dimethyl-6-oxo-4H-4-oxo-naphtho/2,3-b/pyran-2-yl)benzoic acid.

6. A differentiation-inducing agent for neoplastic cells, comprising as active ingredient one or more flavone carboxylic acid compounds of claim 1.

7. The agent of claim 6, wherein the neoplastic cells are leukemia cells.

* * * * *

UNITED STATES PATENT AND TRADEMARK OFFICE
CERTIFICATE OF CORRECTION

PATENT NO. : 4,831,052

DATED : May 16, 1989

INVENTOR(S) : Koichi Shudo

It is certified that error appears in the above-identified patent and that said Letters Patent is hereby corrected as shown below:

Col. 1, line 23; "literature)." should read -- literature)). --

Col. 3, line 65; "(Cells 14,533" should read -- (Cells) 14, 533 --

Col. 4, line 7; "keratiniztion" should read -- keratinization --

Col. 4, line 11; "Mol Those" should read -- Mol. Those --

Col. 4, line 15; "hydrogen;" should read -- hydrogen, --

Col. 5, line 39; "$R_3$" first occurence should read -- $R_2$ --

Col. 8, line 42; "in" should read -- with --

Col. 8, line 47; "$R_3=(CH_3)_2CCH_2(CH_3)_2$," should read

-- $R_2=(CH_3)_2CCH_2CH_2C(CH_3)_2$, --

Col. 9, line 49; "propeny" should read -- propenyl --

Signed and Sealed this

Fifteenth Day of May, 1990

*Attest:*

HARRY F. MANBECK, JR.

*Attesting Officer*  *Commissioner of Patents and Trademarks*